(12) United States Patent
Babkin et al.

(10) Patent No.: US 8,740,891 B2
(45) Date of Patent: Jun. 3, 2014

(54) FLEXIBLE MULTI-TUBULAR CRYOPROBE

(75) Inventors: Alexei V. Babkin, Albuquerque, NM (US); Peter J. Littrup, Bloomfield Hills, MI (US); Robert V. Duncan, Columbia, MO (US); William J. Nydam, Rancho Santa Fe, CA (US)

(73) Assignee: Endocare, Inc., Austin, TX (US)

( * ) Notice: Subject to any disclaimer, the term of this patent is extended or adjusted under 35 U.S.C. 154(b) by 1048 days.

(21) Appl. No.: 12/744,001

(22) PCT Filed: Nov. 19, 2008

(86) PCT No.: PCT/US2008/084004
§ 371 (c)(1),
(2), (4) Date: Jul. 29, 2010

(87) PCT Pub. No.: WO2009/067497
PCT Pub. Date: May 28, 2009

(65) Prior Publication Data
US 2011/0040297 A1 Feb. 17, 2011

Related U.S. Application Data

(60) Provisional application No. 60/989,776, filed on Nov. 21, 2007.

(51) Int. Cl.
*A61B 18/18* (2006.01)
(52) U.S. Cl.
USPC .................... 606/23; 606/20; 606/21; 606/22
(58) Field of Classification Search
USPC ...................................... 606/20–26
See application file for complete search history.

(56) References Cited

U.S. PATENT DOCUMENTS

| 5,037,395 A | 8/1991 | Spencer |
| 5,108,390 A | 4/1992 | Potocky |

(Continued)

FOREIGN PATENT DOCUMENTS

WO WO2005/063136 7/2005

OTHER PUBLICATIONS

Gage AA, Baust J; Mechanisms of Tissue Injury in Cryosurgery; Cryobiology 37; (1998) 171-186; Article CY982115; Academic Press.

(Continued)

*Primary Examiner* — Linda Dvorak
*Assistant Examiner* — Jaymi Della
(74) *Attorney, Agent, or Firm* — Lawrence N. Ginsberg

(57) ABSTRACT

A flexible multi-tubular cryoprobe, including a housing for receiving an inlet flow of near critical cryogenic fluid from a fluid source and for discharging an outlet flow of the cryogenic fluid. A plurality of fluid transfer tubes are securely attached to the housing. This includes a set of inlet fluid transfer tubes for receiving the inlet flow from the housing; and, a set of outlet fluid transfer tubes for discharging the outlet flow to the housing. Each of the fluid transfer tubes is formed of material that maintains flexibility in a full range of temperatures from −200° C. to ambient temperature. Each fluid transfer tube has an inside diameter in a range of between about 0.10 mm and 1.0 mm and a wall thickness in a range of between about 0.01 mm and 0.30 mm. An end cap is positioned at the ends of the plurality of fluid transfer tubes to provide fluid transfer from the inlet fluid transfer tubes to the outlet fluid transfer tubes.

15 Claims, 4 Drawing Sheets

(56) References Cited

U.S. PATENT DOCUMENTS

| | | | |
|---|---|---|---|
| 5,400,602 A | 3/1995 | Chang | |
| 5,520,682 A | 5/1996 | Baust | |
| 5,573,532 A | 11/1996 | Chang | |
| 5,957,963 A | 9/1999 | Dobak | |
| 6,106,518 A * | 8/2000 | Wittenberger et al. | 606/23 |
| 6,161,543 A | 12/2000 | Cox | |
| 6,241,722 B1 | 6/2001 | Dobak | |
| 6,355,029 B1 | 3/2002 | Joye | |
| 6,520,933 B1 * | 2/2003 | Evans et al. | 604/103.07 |
| 6,537,271 B1 | 3/2003 | Murray | |
| 6,551,309 B1 | 4/2003 | Lipivert | |
| 6,685,720 B1 | 2/2004 | Wu | |
| 6,726,653 B2 | 4/2004 | Noda | |
| 6,767,346 B2 | 7/2004 | Damasco | |
| 6,893,419 B2 | 5/2005 | Noda | |
| 6,893,433 B2 | 5/2005 | Lentz | |
| 6,936,045 B2 | 8/2005 | Yu | |
| 6,989,009 B2 | 1/2006 | Lafontaine | |
| 7,022,120 B2 | 4/2006 | Lafontaine | |
| 7,083,612 B2 | 8/2006 | Littrup | |
| 7,220,252 B2 | 5/2007 | Shah | |
| 7,220,257 B1 | 5/2007 | Lafontaine | |
| 7,273,479 B2 | 9/2007 | Littrup | |
| 7,410,484 B2 | 8/2008 | Littrup | |
| 2001/0047134 A1 | 11/2001 | Holdaway | |
| 2002/0049409 A1 * | 4/2002 | Noda et al. | 604/113 |
| 2003/0055415 A1 * | 3/2003 | Yu et al. | 606/21 |
| 2004/0148004 A1 | 7/2004 | Wallsten | |
| 2005/0209587 A1 | 9/2005 | Joye | |
| 2006/0212028 A1 | 9/2006 | Joye | |
| 2006/0235375 A1 * | 10/2006 | Littrup et al. | 606/21 |
| 2006/0247611 A1 | 11/2006 | Abboud | |
| 2006/0253114 A1 | 11/2006 | Saadat | |
| 2008/0312644 A1 * | 12/2008 | Fourkas et al. | 606/22 |

OTHER PUBLICATIONS

Hoffmann NE, Bischof JC; The Cryobiology of Cryosurgical Injury; Urology 60; (2002) 40-49; Elsevier Science Inc.

Gage AA, Baust J.: Mechanisms of tissue injury in cryosurgery. Cryobiology. 1998;37:171-186; and, Hoffmann NE, Bischof JC: The cryobiology of cryosurgical injury. Urology 2002;60;40-49.

International Application No. PCT/US2008/084004 International Search Report and Written Opinion Dated Jan. 14, 2009 Attached to International Publication No. WO2009/067497.

Supplementary European Search Report Regarding Application No. EP08852254 Dated Nov. 19, 2010.

* cited by examiner

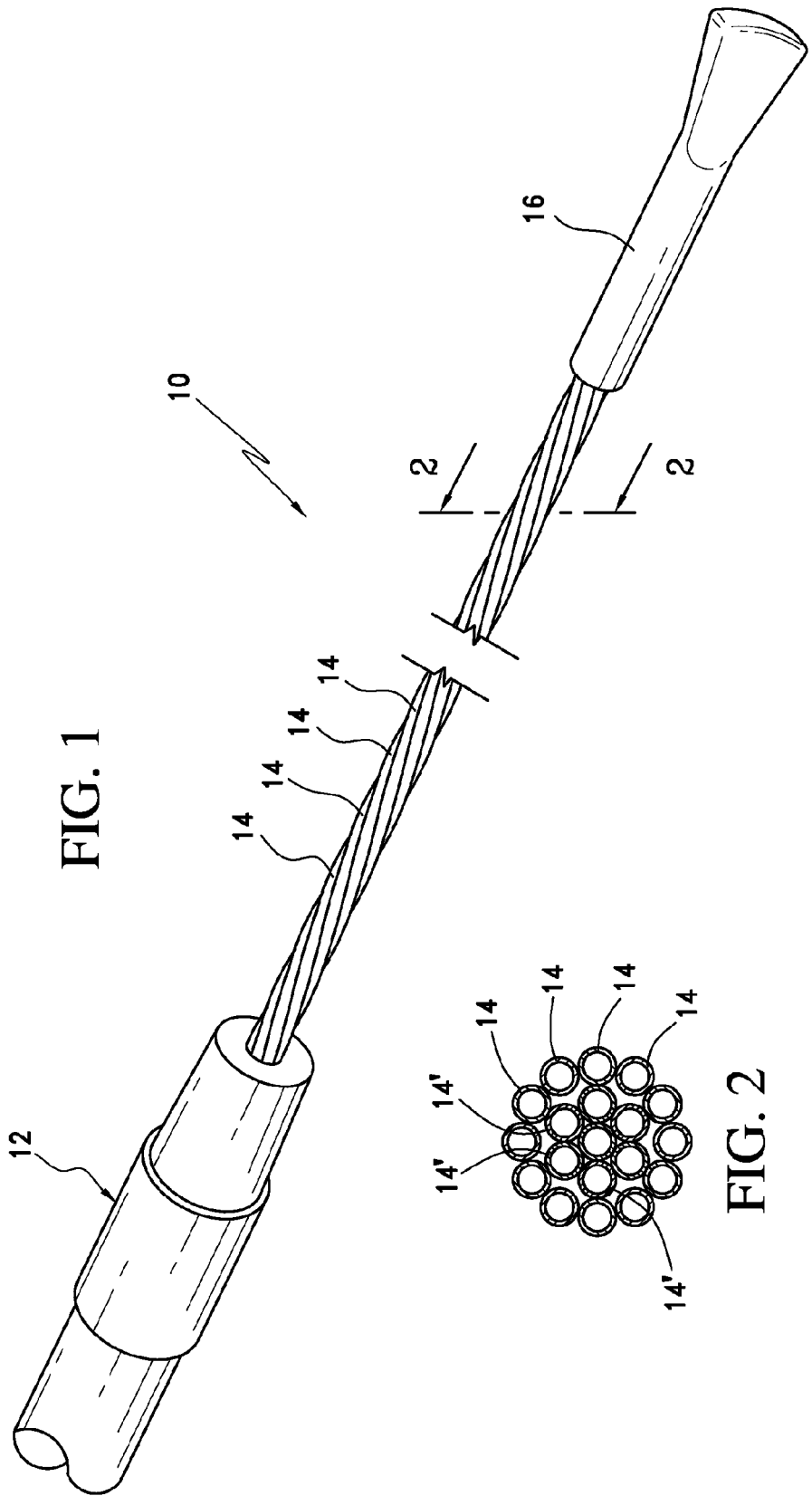

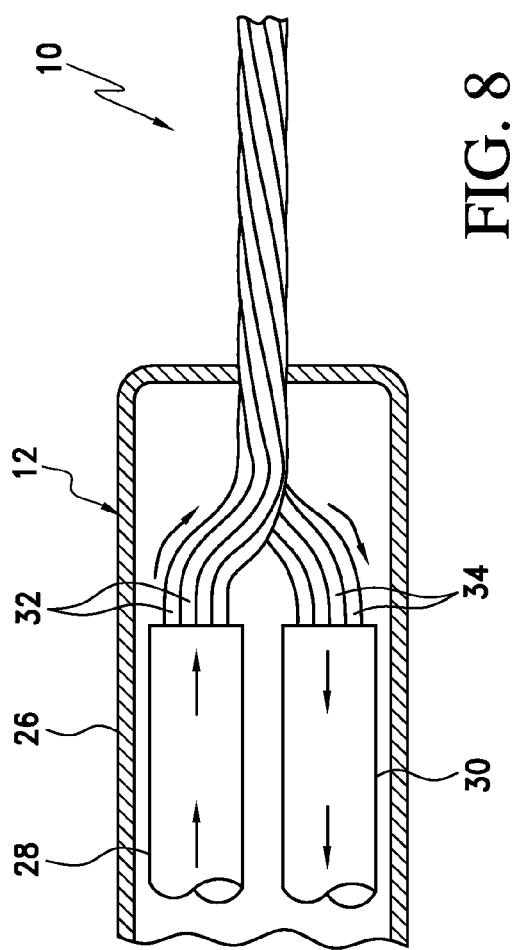
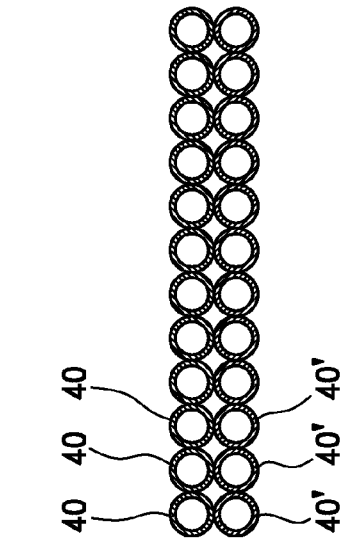
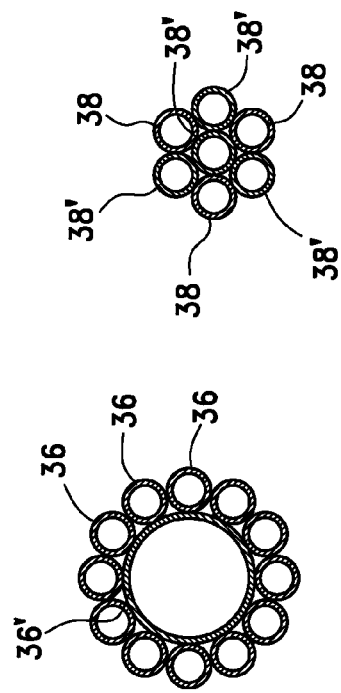
FIG. 8
FIG. 9
FIG. 10
FIG. 11

FLEXIBLE MULTI-TUBULAR CRYOPROBE

CROSS REFERENCE TO RELATED APPLICATIONS

This application is a national stage of International Application No. PCT/US2008/084004, filed Nov. 19, 2008, which claims the benefit of U.S. Provisional Application Ser. No. 60/989,776, filed Nov. 21, 2007. The entire contents of each application are hereby incorporated herein by reference in their entirety.

BACKGROUND OF THE INVENTION

1. Field of the Invention

This invention relates to cryosurgical probes and more particularly to a cryoablation probe with enhanced flexibility under conditions of near critical nitrogen.

2. Description of the Related Art

Cryoablation probes ("Cryoprobes") are used to treat a variety of diseases. Cryoablation probes quickly freeze body tissue, causing the tissue to die after which it will be absorbed by the body, expelled by the body, sloughed off or replaced by scar tissue. Cryothermal treatment is currently used to treat prostate cancer and benign prostate disease, breast tumors including breast cancer, cancerous tumors of the liver, lung, kidney, soft tissues, as well as glaucoma and other eye diseases. Cryoablation may also be used for the treatment of a number of other diseases and conditions including the treatment of cardiac arrhythmias, such as atrial fibrillation. In addition, endovascular and endoscopic uses of cryotherapy are emerging for vascular and cancerous conditions.

During open surgeries, any suitable cryoprobe with enhanced flexibility may used to greater assist destruction of any undesirable tissue. Currently, open surgery for cancer is limited by stiff metal probes, or needles, which have limited their placement into the tumor, or can only be placed on the tumor surface with a disc-like applicator. A suitable probe that could conform to a surgeon's hand, or other operative equipment, would greatly expand tumor access and cryoablation applications. For chest surgery, transmural cryo-lesions can be created on or in the heart to treat cardiac arrhythmia (including atrial fibrillation). A suitable cryoprobe would be useful for this application. Due to the nature of the procedure and anatomical locations that lesions must be placed, the cryoprobe must be sufficiently flexible by the surgeon to be placed on the correct location of the heart surface.

Although a rigid probe can be provided with a predetermined shape, one must select a probe that has the most appropriate shape for positioning the working portion of the probe in contact with the treatment site in view of the particular anatomical pathway to be followed in the patient. It will be appreciated that a large inventory of rigid probes may be required to accommodate the various treatment sites and patient anatomies. Further, for a patient having a relatively uncommon anatomic configuration and/or a difficult to reach treatment site, all rigid probes of an existing set may have less than optimal shapes for positioning. This may impair the prospects of successfully carrying out the treatment procedure, especially when the treatment is one such as an ablation treatment that relies on good tissue contact and operates locally upon the contacted tissue. For an ablation probe which must bear against tissue at the remote region to ablate a lesion, the contour followed by the probe in reaching the target site will in general further restrict the direction and magnitude of the movement and forces which may be applied or exerted on the working portion of the device to effect tissue contact and treatment.

The prior art includes references to malleable and flexible cryoprobes. For example, U.S. Pat. No. 6,161,543, issued to Cox et al, discloses the use of a malleable probe. The probe has a malleable shaft. A malleable metal rod is coextruded with a polymer to form the shaft. The rod permits the user to shape the shaft as necessary so that a tip can reach the tissue to be ablated.

U.S. Pat. No. 5,108,390, issued to Potocky et al, discloses a highly flexible cryoprobe that can be passed through a blood vessel and into the heart without external guidance other than the blood vessel itself.

Several patents disclose the use of bellows-type assemblies for use with cryoablation systems. For example, U.S. Pat. No. 6,241,722, issued to Dobak et al, discloses a cryogenic catheter with a bellows and which utilizes a longitudinally movable Joule-Thomson nozzle of expansion. The Dobak '722 device preferably uses closed media-flow pathways for efficient recycling of the media employed.

Dobak et al, in U.S. Pat. No. 5,957,963, disclose the used of a flexible catheter inserted through the vascular system of a patient to place the distal tip of the catheter in an artery feeding a selected organ of the patient. The '963 patent discloses a heat transfer bellows for cooling the blood flowing through the artery.

U.S. Pat. No. 6,767,346, issued to Damasco et al, entitled, "Cryosurgical Probe With Bellows Shaft", discloses use of a cryosurgical probe with a bellows shaft. U.S. Pat. No. 6,936,045, issued to Yu et al, entitled, "Malleable Cryosurgical Probe" discloses a cryosurgical probe used for Joule-Thomson nozzles.

CryoCath Technologies, Inc., Montreal, Quebec, Canada, utilizes a cryoablation probe trademarked under the name Surgifrost® which involves the use of a cryoprobe with a malleable or corrugated shell. A problem with this and other similar products is that these cryoprobes are not sufficiently flexible for optimum use and still retain memory. As a result, there is often an incomplete/intermittent thermal contact along the whole line of freezing. The small contact area provides a limitation for the power delivered to the tissue.

SUMMARY

The present invention is a flexible multi-tubular cryoprobe, including a housing for receiving an inlet flow of cryogenic fluid from a fluid source and for discharging an outlet flow of the cryogenic fluid. A plurality of fluid transfer tubes are securely attached to the housing. This includes a set of inlet fluid transfer tubes for receiving the inlet flow from the housing; and, a set of outlet fluid transfer tubes for discharging the outlet flow to the housing. Each of the fluid transfer tubes is formed of material that maintains flexibility in a full range of temperatures from −200° C. to ambient temperature. Each fluid transfer tube has an inside diameter in a range of between about 0.10 mm and 1.0 mm and a wall thickness in a range of between about 0.01 mm and 0.30 mm. An end cap is positioned at the ends of the plurality of fluid transfer tubes to provide fluid transfer from the inlet fluid transfer tubes to the outlet fluid transfer tubes.

The present cryoprobe has much more flexibility than prior art cryoablation probes. As a result of this enhanced flexibility there is better thermal management and a more uniform freeze. Additionally, there is a significantly larger surface area. As a result there are shorter freeze times, a deeper freeze, and the ability to reduce the size of the cryoprobe.

As will be disclosed below, the present invention has a variety of potential applications. It can be utilized for external and internal cardiac applications, endovascular applications, endoscopic applications, surgical tools used laparoscopically or with surgical robotic devices, fat ablation and subcutaneous tissue sculpting.

Other objects, advantages, and novel features will become apparent from the following detailed description of the invention when considered in conjunction with the accompanying drawings.

BRIEF DESCRIPTION OF THE DRAWINGS

FIG. 1 is a perspective view of a preferred embodiment of the cryoprobe of the present invention.

FIG. 2 is a view taken along line 2-2 of FIG. 1.

FIG. 8 is a schematic illustration of one embodiment in which the housing includes a handle.

FIG. 9 illustrates a tube configuration with twelve inlet fluid transfer tubes.

FIG. 10 illustrates an alternate tube configuration with three inlet fluid transfer tubes and four outlet fluid transfer tubes.

FIG. 11 illustrates an alternate tube configuration with a plane of inlet fluid transfer tubes adjacent to a plane of outlet fluid transfer tubes.

DETAILED DESCRIPTION OF THE INVENTION

Figure 3:
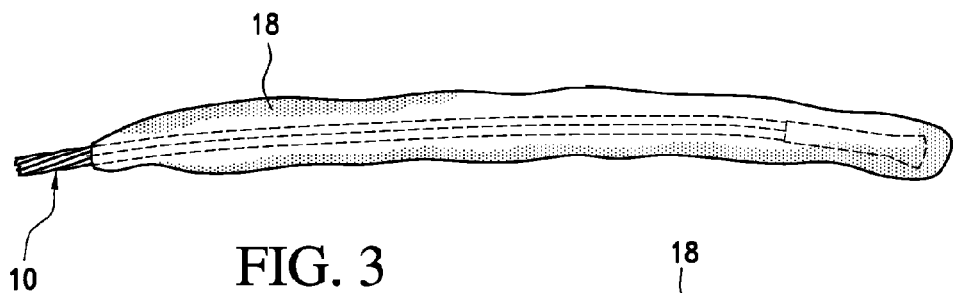
FIG. 3 is a perspective view of cryoprobe of FIG. 1 operated to generate an iceball.

Referring to the drawings and the characters of reference marked thereon FIGS. 1 and 2 illustrate a preferred embodiment of the flexible multi-tubular cryoprobe of the present invention, designated generally as 10. The cryoprobe 10 includes a housing 12 for receiving an inlet flow of near critical cryogenic fluid from a fluid source (not shown) and for discharging an outlet flow of the cryogenic fluid. A plurality of fluid transfer tubes 14, 14' are securely attached to the housing 12. These tubes include a set of inlet fluid transfer tubes 14 for receiving the inlet flow from the housing; and, a set of outlet fluid transfer tubes 14' for discharging the outlet flow to the housing 12. Each of the fluid transfer tubes 14, 14' is formed of material that maintains flexibility in a full range of temperatures from −200° C. to ambient temperature. Each fluid transfer tube has an inside diameter in a range of between about 0.10 mm and 1.0 mm (preferably between about 0.20 mm and 0.50 mm). Each fluid transfer tube has a wall thickness in a range of between about 0.01 mm and 0.30 mm (preferably between about 0.02 mm and 0.10 mm). An end cap 16 is positioned at the ends of the fluid transfer tubes 14, 14' to provide fluid transfer from the inlet fluid transfer tubes 14 to the outlet fluid transfer tubes 14'.

The tubes 14, 14' are preferably formed of annealed stainless steel or a polyimide, preferably a KAPTON® polyimide material. It is necessary that the material maintains flexibility at a near critical temperature.

As used herein the term "flexibility" refers to the ability of the cryoprobe to be bent in the orientation desired by the user without applying excess force and without fracturing or resulting in significant performance degradation.

The cryogenic fluid utilized is preferably near critical nitrogen. However, other near critical cryogenic fluids may be utilized such as argon, neon, helium or others. As used herein, the term "near critical" refers to the liquid-vapor critical point, which is the relevant critical point to this invention. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. In other words, reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

The fluid source for the cryogenic fluid may be provided from a suitable mechanical pump or a non-mechanical critical cryogen generator. Such fluid sources are disclosed in, for example, U.S. patent application Ser. No. 10/757,768 which issued as U.S. Pat. No. 7,410,484, on Aug. 12, 2008 entitled "CRYOTHERAPY PROBE", filed Jan. 14, 2004 by Peter J. Littrup et al.; U.S. patent application Ser. No. 10/757,769 which issued as U.S. Pat. No. 7,083,612 on Aug. 1, 2006, entitled "CRYOTHERAPY SYSTEM", filed Jan. 14, 2004 by Peter J. Littrup et al.; U.S. patent application Ser. No. 10/952,531 which issued as U.S. Pat. No. 7,273,479 on Sep. 25, 2007 entitled "METHODS AND SYSTEMS FOR CRYOGENIC COOLING" filed Sep. 27, 2004 by Peter J. Littrup et al. U.S. Pat. No. 7,410,484, U.S. Pat. No. 7,083,612 and U.S. Pat. No. 7,273,479 are incorporated herein by reference, in their entireties, for all purposes.

The endcap 16 may be any suitable element for providing fluid transfer from the inlet fluid transfer tubes to the outlet fluid transfer tubes.

There are many configurations for tube arrangements. In one class of embodiments the tubes are formed of a circular array, wherein the set of inlet fluid transfer tubes comprises at least one inlet fluid transfer tube defining a central region of a circle and wherein the set of outlet fluid transfer tubes comprises a plurality of outlet fluid transfer tubes spaced about the central region in a circular pattern. In the configuration shown in FIG. 2, the tubes 14, 14' fall within this class of embodiments.

During operation, the cryogen fluid arrives at the cryoprobe through a supply line from a suitable nitrogen source at a temperature close to −200° C., is circulated through the multi-tubular freezing zone provided by the exposed fluid transfer tubes, and returns to the housing.

It is essential that the nitrogen flow not form gaseous bubbles inside the small diameter tubes under any heat load, so as to not create a vapor lock that limits the flow and the cooling power. By operating at the near critical condition the vapor lock is eliminated as the distinction between the liquid and gaseous phases disappears.

The present invention provides a substantial increase in the heat exchange area between the cryogen and tissue, over prior art cryoprobes, by this multi-tubular design. Depending on the number of tubes used, the present cryoprobes can increase the contact area several times over previous cryoprobes having similarly sized diameters with single shafts.

Figure 4:
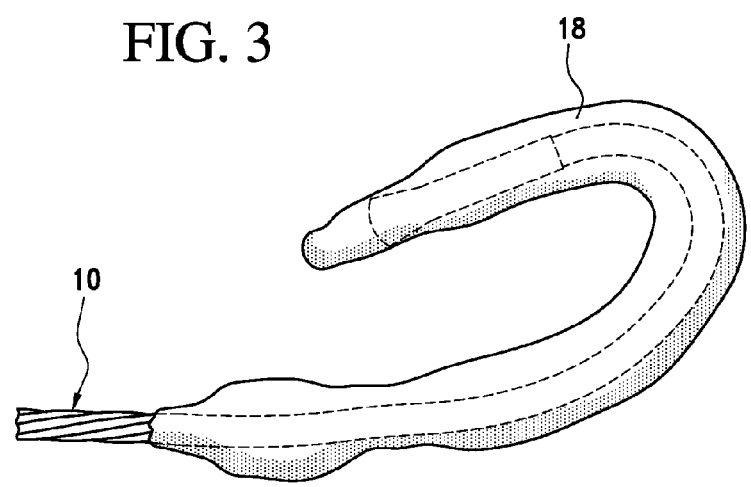
FIG. 4 is a perspective view of the cryoprobe of FIG. 1 that is bent to approximately 180° to form a commensurately bent iceball.
Figure 5:
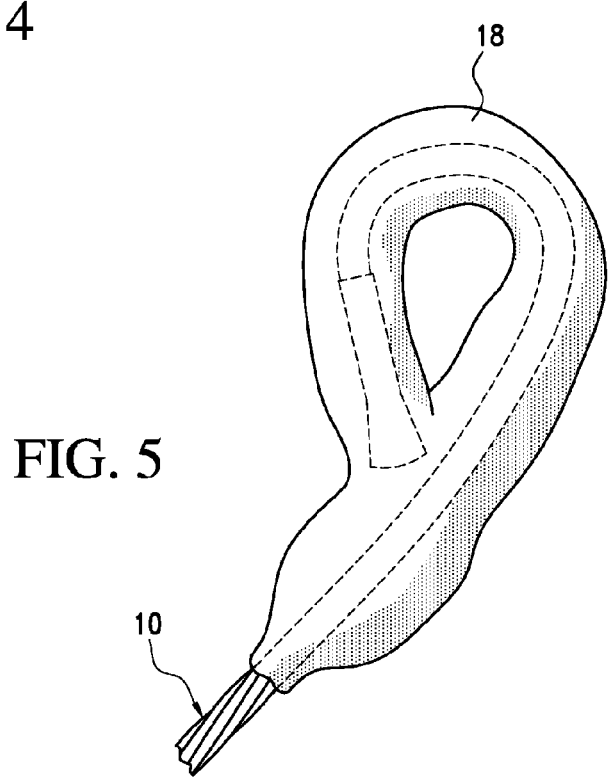
FIG. 5 illustrates the cryoprobe sufficiently bent so as to form a loop.

As can be seen in FIG. 3, an iceball 18 is generated about the cryoprobe 10. Referring now to FIG. 4, it can be seen that an iceball 18 can be created in the desired shape by bending the cryoprobe in the desired orientation. A complete iceball 18 loop can be formed, as shown in FIG. 5.

Figures 6, 7:
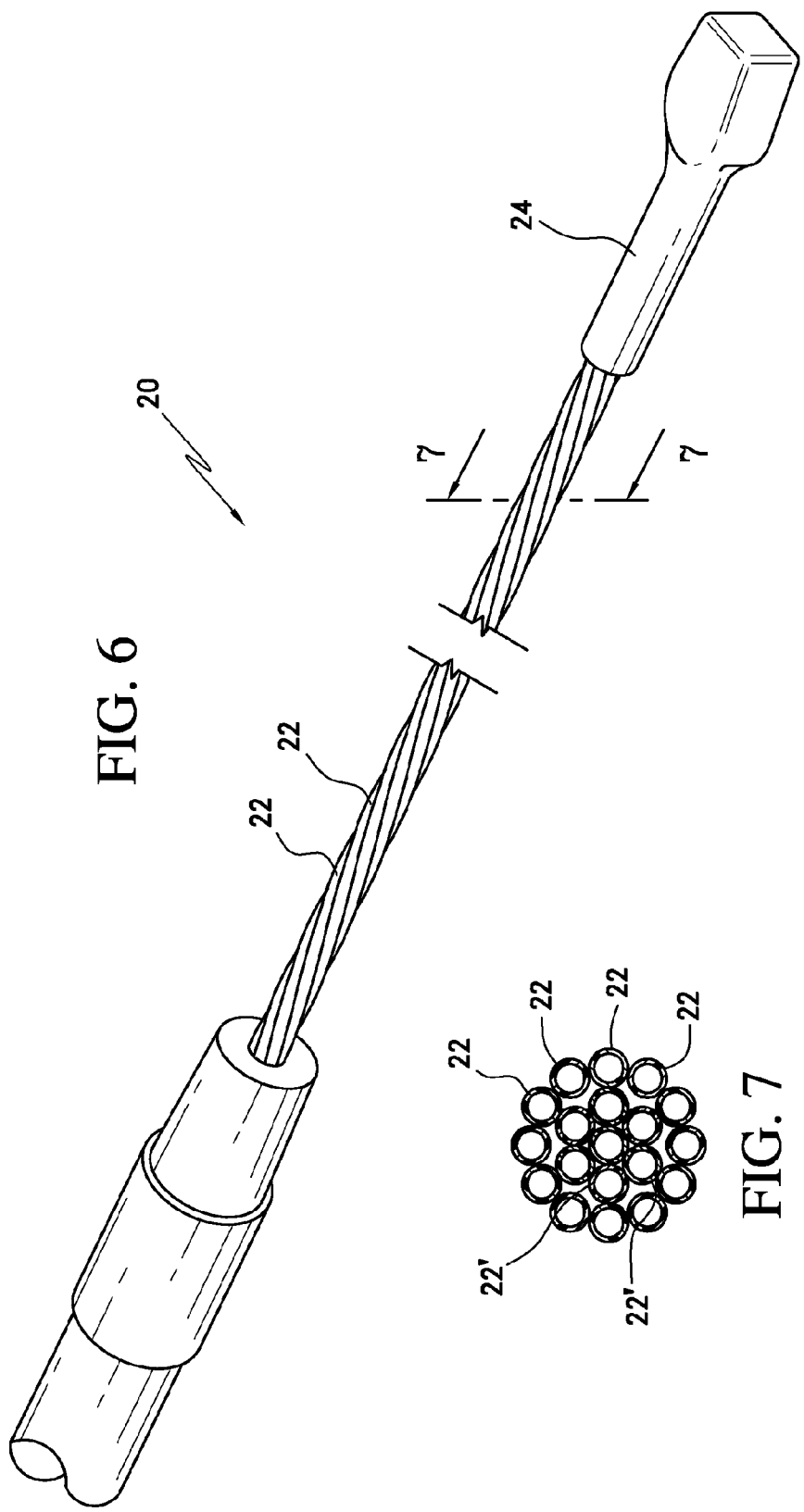
FIG. 6 is a perspective view of a second embodiment of the present invention utilizing polyimide as the tubing material.
FIG. 7 is a view taken along line 7-7 of FIG. 6.

Referring now to FIG. 6, a cryoprobe 20 is illustrated, which is similar to the embodiment of FIG. 1, however, with this embodiment a polyimide material is used to form the tubes 22, 22'. Furthermore, this figure illustrates the use of a clamp 24 as an endcap.

Referring now to FIG. 8, one embodiment of the housing 12 of a cryoprobe 10 is illustrated. The housing 12 includes a handle 26 that supports an inlet shaft 28 and an outlet shaft 30. The inlet shaft 28 is supported within the handle 26 for containing proximal portions of the set of inlet fluid transfer tubes 32. The outlet shaft 30 is supported within the handle 26 for containing proximal portions of the set of outlet fluid transfer tubes 34. Both of the shafts 28, 30 include some type of thermal insulation, preferably a vacuum, to isolate them.

Referring now to FIGS. 9-11 various configurations of tube configurations are illustrated. In FIG. 9 a configuration is illustrated in which twelve inlet fluid transfer tubes 36 circumscribe a single relatively large outlet fluid transfer tube 36'. In FIG. 10, three inlet fluid transfer tubes 38 are utilized with four outlet fluid transfer tubes 38'. In FIG. 11, a plane of inlet fluid transfer tubes 40 are formed adjacent to a plane of outlet of fluid transfer tubes 40'.

Example 1

In a first example, an annealed stainless steel cryoprobe was utilized with twelve fluid transfer tubes. There were six inlet fluid transfer tubes in the outer circumference and six outlet fluid transfer tubes in the center. The tubes were braided as shown in FIG. 1. The length of the freeze zone was 6.5 inches. Each fluid transfer tube had an outside diameter of 0.16 inch and an inside diameter 0.010 inch. The diameter of the resultant array of tubes was 0.075 inch. After a one minute freeze in 22° C. water and near-critical (500 psig) nitrogen flow of approximately 20 STP l/min, ice covered the entire freeze zone of the flexible cryoprobe with an average diameter of about 0.55 inch. After four minutes the diameter was close to 0.8 inch. The warm cryoprobe could be easily bent to any shape including a full loop of approximately 2 inch in diameter without any noticeable change in its cooling power.

Example 2

In a second example, a polyimide cryoprobe was utilized with twenty-one fluid transfer tubes. There were ten inlet fluid transfer tubes in the outer circumference and eleven outlet fluid transfer tubes in the center. The tubes were braided. The length of the freeze zone was 6.0 inches. Each fluid transfer tube had an outside diameter of 0.0104 inch and an inside diameter 0.0085 inch. Each tube was pressure rated for about 1900 psig (working pressure 500 psig). The average diameter of the flexible portion of the cryoprobe was 1.15 mm (0.045 inch). The cryoprobe was extremely flexible with no perceivable "memory" in it. It bent by its own weight of just 1 gram and easily assumed any shape with a bending radius as little as 0.1 inch, including a 1 inch diameter "knot". A full loop was created with the cryoprobe. After a one minute freeze in 22° C. water and near critical (500 psig) nitrogen flow of approximately 20 STP l/min, ice covered the entire freeze zone of the flexible cryoprobe with an average diameter of 0.65 inch and in two minutes it closed the entire 1 inch hole inside the loop.

The applications of the present inventive concepts are far reaching. The ability to have a flexible catheter (i.e. cryoprobe) extends cryotherapy from a rigid needle-like application to nearly any current device used to assist current diagnostic and therapeutic procedures. While endovascular uses are a primary consideration, this also applies to endoscopic, open surgical, subcutaneous and superficial dermatologic applications. These all relate to application of ablative temperatures at a tissue interface, generally requiring temperatures of approximately −30 C (see, e.g. Gage A A, Baust J.: Mechanisms of tissue injury in cryosurgery. Cryobiology. 1998; 37:171-186; and, Hoffmann N E, Bischof J C: The cryobiology of cryosurgical injury. Urology 2002; 60:40-49). The following are potential applications of the technology of the present invention:

External cardiac applications: The external cardiac application involves use of a rope-like array that can encircle the heart at any desired configuration, allowing more tailored use around the circumference of the pulmonary veins. Since the inlet of the pulmonary veins in the left atrium is the site for most correctable arrythmias, improved isolation of the pulmonary vein ostia by cryoablation approaches the function of the surgical cardiac Maze procedure. In addition, the same 'rope' design can be held in place within an insulated angled applicator, allowing direct pressure applications of cryotherapy energy to create linear ablations. These ablation lines can then be used to connect the circular paths around the pulmonary veins, producing a thorough ablation pattern that closely mimics the suture lines of the Maze and its resultant high success rate in stopping arrhythmias. Perhaps more important, the greater power and surface areas afforded by the rope-design allow demonstration of full thickness ablation on a beating heart.

Internal cardiac application: The development of multiple endovascular products is now possible since the pressure of near-critical nitrogen falls below the maximum tolerance of ~600 psi for endovascular catheter material. A cardiac ablation catheter in accordance with the principals of the present invention can be placed in direct contact along the internal lining of the left atrium, thereby avoiding most of the massive heat-sink of flowing blood inside the heart as the ablation proceeds outward. The above noted external ablation device would have higher power demands in order to achieve full thickness ablation of the myocardium, having to freeze from outside the heart into the high heat-sink of the pumping blood left atrium. Therefore, all necessary catheter configurations could be conceived which provide both the circumferential, as well as linear, ablations to mimic the surgical Maze procedure noted above.

Endovascular applications: Some manufacturers of endovascular catheters for balloon dilatations utilize nitrous oxide because its pressure for Joule-Thomson function is still less than the ~600 psi of maximal catheter tolerance (see, for example, U.S. Pat. No. 6,989,009, entitled "Cryo Balloon", issued Jan. 24, 2006 to D. M. Lafontaine). Other uses of cryoplasty (i.e., cryo-balloon angioplasty) involve letting circulating liquid nitrous oxide evaporate in the balloon, driving balloon temps down to ~−80 C. The biology of reducing stenosis following cryoplasty appears related to preventing formation of the scar tissue that forms along the vessel walls. The temperatures rapidly drop away from the balloon surface, reaching temperatures within the artery wall of no lower than −20 C. This produces primarily only apoptosis of the fibroblasts without necrosis of the smooth muscle in the vessel wall. However, even more powerful cryogens such as near critical nitrogen could produce more thorough prevention of fibroblast formation of scar. In addition, such transmural wall necrosis would not disrupt the collagen or weaken the vessel wall as demonstrated by the safety of cardiac ablation. Treatment of early aneurysm formation by full thickness wall necrosis would nevertheless cause fibrosis of the surrounding perivascular space, effectively strengthening the vessel wall. A new treatment for early aneurysm formation in this manner could avoid the foreign body of stents after the aneurysm has already become too big.

Endoscopic applications: The uses of endoscopic cryotherapy may be deemed to be best demonstrated by the extensive body of work by Dr. Maiwand in treating endobronchial tumors. The safety of cryotherapy in causing much less perforation than heat-based ablations would extend the use of cryotherapy even further out in the bronchial tree if an appropriate catheter with high flexibility were available. Lung cancer is much more common than GI tumors but endoscopic uses could also be envisioned for both upper and lower GI endoscopy. Finally, endoscopic access for head and neck surgery may be more feasible with a flexible endoscopic catheter.

Surgical tools: Many tumors that are directly visible by both open surgery and laparoscopy could be better addressed by a flexible system that conforms to, or mimics, the flexibility of the hand, or even robotic articulating devices (e.g., DaVinci robotic surgeries). The flexible design of multiple flexible filaments (i.e. fluid transfer tubes) could be distributed over insulated surfaces that could be in contact with the hand. A 3-4 fingered system could thus grasp a tumor and provide a rapid circumferential tumor freeze with greater control and less morbidity than a direct puncture with multiple needle probes. The greater power capacity of near-critical nitrogen should thus allow a tumor of up to 4 cm to be thoroughly frozen (i.e., 'outside-in') by grasping it with a 4-fingertip system. This would cover most tumors encountered during surgical exploration but could be used to cover larger tumors in sequential freezes. A system mimicking a 3-5 'fingered' grasping approach could thus be envisioned for surgical tools used laparoscopically or with surgical robotic devices.

Radiological Applications: Ablations are now requiring multiple cryoprobes to generate sufficiently lethal isotherms to destroy most tumors over 1 cm. However, the procedure may be simplified by a diverging array of tiny needles projecting out the main needle tip (e.g., Starburst configuration of Rita Medical Systems' RF probe). The tiny channels of cryogen flow permitted by near critical nitrogen would allow the total diameter main needle to be no more than 3 mm, yet have up to 10 diverging tiny needles projecting into the tissue for maximal production. Therefore, a much larger and colder ice ball would then be possible for any cryoprobe, compared with a straight cryoprobe of similar size. Therefore, even a small needle of only ~1 mm outer diameter may still have 3-4 tiny prongs extending into tissue causing better delivery of cold into surrounding tissues.

Dermatology/plastic surgery: Flexible needles may now be possible that allow initial insertion with a stiff tip but a flexible shaft. The final probe configuration could thus be better sculpted to the shape of the tissue to be ablated. This may have exemplary applications for fat ablation and subcutaneous tissue sculpting.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent is:

1. A flexible multi-tubular cryoprobe, comprising:
a) a housing for receiving an inlet flow of near critical cryogenic fluid from a near critical cryogenic fluid source and for discharging an outlet flow of said near critical cryogenic fluid;
b) a plurality of fluid transfer tubes arranged in a circular array and securely attached to said housing, comprising a set of inlet fluid transfer tubes for receiving said inlet flow from said housing; and, a set of outlet fluid transfer tubes for discharging said outlet flow to said housing, each of said plurality of fluid transfer tubes being formed of material that maintains flexibility in a full range of temperatures from −200° C. to ambient temperature, each of said plurality of fluid transfer tubes having an inside diameter in a range of between about 0.10 mm and 1.0 mm; each of said plurality of fluid transfer tubes having a wall thickness in a range of between about 0.01 mm and 0.30 mm; and,
c) an end cap positioned at distal ends of said plurality of fluid transfer tubes to provide fluid transfer from said set of inlet fluid transfer tubes to said set of outlet fluid transfer tubes
wherein said set of inlet fluid transfer tubes comprises a plurality of inlet fluid transfer tubes located along a circumference of the circular array in order to contact target tissue thereby increasing a heat exchange area between said near critical cryogenic fluid and said target tissue,
wherein said set of outlet fluid transfer tubes comprises a plurality of outlet fluid transfer tubes located on an interior of the circular array in order to be shielded from contact with said target tissue by said plurality of inlet fluid transfer tubes, and
wherein said circular array of said plurality of fluid transfer tubes is formed within said housing at a distance away from a distal-most end of said housing.

2. The flexible multi-tubular cryoprobe of claim 1, wherein said material that forms said plurality of fluid transfer tubes comprises annealed stainless steel.

3. The flexible multi-tubular cryoprobe of claim 1, wherein said material that forms said plurality of fluid transfer tubes comprises polyimide material.

4. The flexible multi-tubular cryoprobe of claim 1, wherein said material that forms said plurality of fluid transfer tubes comprises a material that maintains flexibility at a near critical nitrogen temperature.

5. The flexible multi-tubular cryoprobe of claim 1, wherein a total number of said plurality of fluid transfer tubes comprising said set of inlet fluid transfer tubes and said set of outlet fluid transfer tubes is 7 to 100.

6. The flexible multi-tubular cryoprobe of claim 1, wherein a total number of said plurality of fluid transfer tubes comprising said set of inlet fluid transfer tubes and said set of outlet fluid transfer tubes is 7 to 50.

7. The flexible multi-tubular cryoprobe of claim 1, wherein said housing, comprises:
a) a handle;
b) an inlet shaft supported within said handle for containing proximal portions of said set of inlet fluid transfer tubes; and,
c) an outlet shaft supported within said handle for containing proximal portions of said set of outlet fluid transfer tubes.

8. A cryosurgical system, comprising:
a) a source of near critical cryogenic fluid; and, b) a flexible multi-tubular cryoprobe, comprising:
  i. a housing for receiving an inlet flow of near critical cryogenic fluid from said source of near critical cryogenic fluid and for discharging an outlet flow of said near critical cryogenic fluid;
  ii. a plurality of fluid transfer tubes arranged in a circular array and securely attached to said housing, comprising a set of inlet fluid transfer tubes for receiving said inlet flow from said housing; and, a set of outlet fluid transfer tubes for discharging said outlet flow to said housing, each of said plurality of fluid transfer tubes being formed of material that maintains flexibility in a full range of temperatures from −200° C. to ambient temperature, each of said plurality of fluid transfer tubes having an inside diameter in a range of between about 0.10 mm and 1.0 mm; each of said plurality of fluid transfer tubes having a wall thickness in a range of between about 0.01 mm and 0.30 mm; and,
  iii. an end cap positioned at distal ends of said plurality of fluid transfer tubes to provide fluid transfer from said set of inlet fluid transfer tubes to said set of outlet fluid transfer tubes
    wherein said set of inlet fluid transfer tubes comprises a plurality of inlet fluid transfer tubes located along a circumference of the circular array in order to contact target tissue thereby increasing a heat exchange area between said near critical cryogenic fluid and said target tissue
  wherein said set of outlet fluid transfer tubes comprises a plurality of outlet fluid transfer tubes located on an interior of the circular array in order to be shielded from contact with said target tissue by said plurality of inlet fluid transfer tubes, and
    wherein said source of near critical cryogenic fluid is directly connected to said set of inlet fluid transfer tubes.

9. The cryosurgical system of claim 8, wherein said source of near critical cryogenic fluid comprises nitrogen.

10. The cryosurgical system of claim 8, wherein said material that forms said plurality of fluid transfer tubes comprises annealed stainless steel.

11. The cryosurgical system of claim 8, wherein said material that forms said plurality of fluid transfer tubes comprises polyimide material.

12. The cryosurgical system of claim 8, wherein said material that forms said plurality of fluid transfer tubes comprises material that maintains flexibility at a near critical nitrogen temperature.

13. The flexible multi-tubular cryoprobe of claim 12, wherein a total number of said plurality of fluid transfer tubes comprising said set of inlet fluid transfer tubes and said set of outlet fluid transfer tubes is 7 to 100.

14. The flexible multi-tubular cryoprobe of claim 12, wherein a total number of said plurality of fluid transfer tubes comprising said set of inlet fluid transfer tubes and said set of outlet fluid transfer tubes is 7 to 50.

15. The cryosurgical system of claim 8, wherein said housing, comprises:
  a) a handle;
  b) an inlet shaft supported within said handle for containing proximal portions of said set of inlet fluid transfer tubes; and,
  c) an outlet shaft supported within said handle for containing proximal portions of said set of outlet fluid transfer tubes.

* * * * *